United States Patent [19]

Asai et al.

[11] Patent Number: 4,791,933
[45] Date of Patent: Dec. 20, 1988

[54] RADIO ELECTROCARDIOGRAPHY FOR A LIVING BODY MOVING IN THE WATER

[75] Inventors: Toshio Asai, Uchinadamachi; Yasuhiro Nakaya, Futakuchimachi; Yasuaki Onodera, Saitamaken, all of Japan

[73] Assignee: Fukuda Denshi Co., Ltd., Tokyo, Japan

[21] Appl. No.: 16,984

[22] Filed: Feb. 19, 1987

Related U.S. Application Data

[63] Continuation of Ser. No. 742,820, Jun. 10, 1985, abandoned.

[30] Foreign Application Priority Data

Jun. 11, 1984 [JP] Japan ................................ 59-120381

[51] Int. Cl.⁴ ............................................... A61B 5/04
[52] U.S. Cl. .................................... 128/640; 128/643; 128/696; 128/903
[58] Field of Search ............... 128/639, 640, 643, 696, 128/710, 903

[56] References Cited

U.S. PATENT DOCUMENTS

| 3,568,663 | 3/1971 | Phipps | 128/643 |
| 3,595,218 | 7/1971 | Kirkpatrick | 128/643 |
| 4,515,162 | 5/1985 | Yamamoto et al. | 128/643 |

FOREIGN PATENT DOCUMENTS

1466834  3/1969  Fed. Rep. of Germany ...... 128/903

Primary Examiner—Edward M. Coven
Assistant Examiner—Randy Citrin
Attorney, Agent, or Firm—Pollock, VandeSande & Priddy

[57] ABSTRACT

A method of diagnosing the heart condition of a living body moving in the water, in which an electrocardiogram recorded by the steps of hermetically contacting electrodes on the skin surface of the body moving under water, detecting an electrocardiac signal by the electrodes, leading the detected electrocardiac signal through lead wires to a wireless transmitter on the living body, remotely receiving the radio electrocardiac signal transmitted from the transmitted by a receiver, and recording the electrocardiogram on the basis of the radio electrocardiac signal received by the receiver.

1 Claim, 3 Drawing Sheets

RADIO ELECTROCARDIOGRAPHY FOR A LIVING BODY MOVING IN THE WATER

This application is a continuation of Ser. No. 742,820, filed on June 10, 1985, now abandoned.

FIELD OF THE INVENTION

The present invention relates to radio electrocardiography used to record an electrocardiogram for indicating the function of a heart of a living body during exercise in the water, such as swimming rehabilitation.

BACKGROUND OF THE INVENTION

As a result of the recent developments in medical techniques and the general medical care of hearts, a number of serious and mild cardiac diseases have been discovered and aided by cardiac therapy. However, mild cardiac patients, particularly cardiac sick infants discovered at the school by cardiac examinations conducted nationwide have been prevented from swimming as being too severe as exercise.

In conventional infant circulatory organ science, the reason that the mild cardiac infant cannot swim safely is the result of consideration of the energy consumption and the result of inspection of an electrocardiogram of the infants on the ground. So far, there has been no electrode for recording the electrocardiogram during swimming. Therefore, the swimming restrictions are not based on the results of the inspection of an electrocardiogram recorded during actual swimming.

However, the circulatory action during swimming is different from that during the exercises on the ground, and abnormal variations are observed during swimming. On the other hand, at present, since accurate circulatory action of a pupil during swimming is unknown, the safety of the mild cardiac sick pupil cannot be confirmed. It is diffucult to give approval for swimming to the mild cardiac sick pupil, based on a conventional inspection.

Consequently, it becomes necessary to prove that the pupil can swim safely based on an electrocardiogram recorded during actual swimming.

In order to record the electrocardiogram of a living body during swimming, it is necessary to put the electrodes on the skin surface of the pupil's body, to connect the electrodes through cables to an electrocardiograph placed on the ground, to let pupil with the electrodes swim, to lead ultrafine current from a heart induced on the skin surface during swimming through the cable to the electrocardiograph placed on the ground, and to measure the variation in the potential generated in the living body by the electrocardiograph.

In case that the electrocardiogram of the living body during swimming is recorded by the electrocardiograph placed on the ground as described above, when the living body swims for a long distance, the cable must be lengthened in response to the swimming distance. As the cable becomes longer, the cost increases, and further, an accurate electrocardiogram cannot be obtained due to leakage of the ultrafine current. Further, there is a problem that the examinee cannot swim freely since the examinee's legs and arms may be caught by the cable.

SUMMARY OF THE INVENTION

It is a primary object of this invention to provide radio electrocardiography that can accurately record an electrocardiogram of a living body while the living body is swimming freely.

According to the present invention, there is provided a radio electrocardiography that can record an electrocardiogram of a living body while swimming, comprising the steps of hermetically contacting electrodes on the surface of the living body, letting the living body swim, detecting an electrocardiac signal by the electrodes, leading the detected electrocardiac signal through lead wires to a wireless transmitter mounted on the living body, receiving the radio electrocardiac signal by a receiver, and recording the electrocardiogram on the basis of the radio electrocardiac signal received by the receiver.

The present invention will be described in detail with reference to the accompanying drawings.

DETAILED DESCRIPTION OF THE INVENTION

Figure 1:
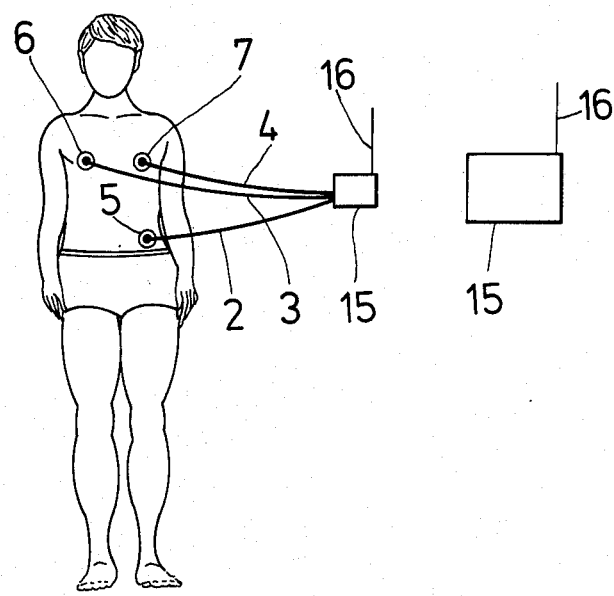
FIG. 1 is an explanatory view for describing a method of remotely receiving an electrocardiac signal by radio wave.

In FIG. 1, which shows a method of remotely receiving an electrocardiac signal by radio wave, reference numerals 5, 6, 7 designate waterproof electrodes. Ends of lead wires 2, 3, 4 are respectively connected to the electrodes 5, 6, 7, the other ends of wires 2, 3, 4 being connected to transmitter 15 for generating a radio wave signal.

Figure 3:
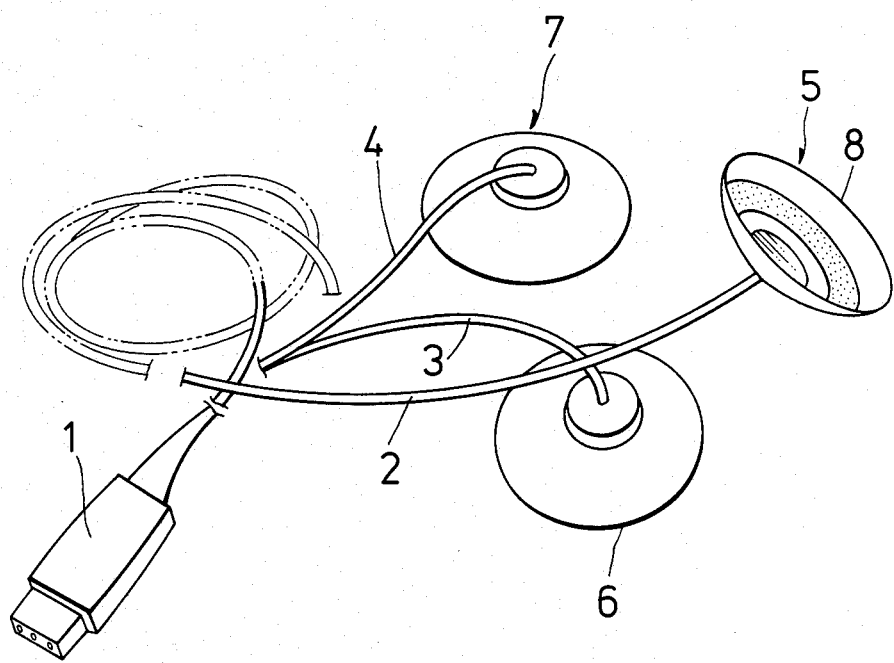
FIG. 3 is a perspective view showing combination of electrodes and lead wires.
Figure 4:
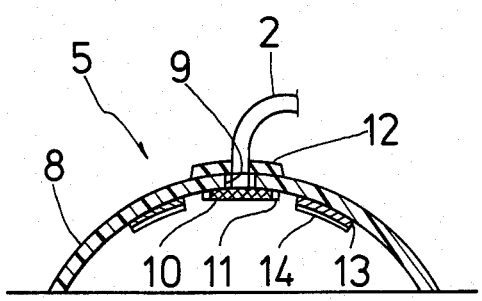
FIG. 4 is a longitudinal sectional view of an electrode.
Figure 5:
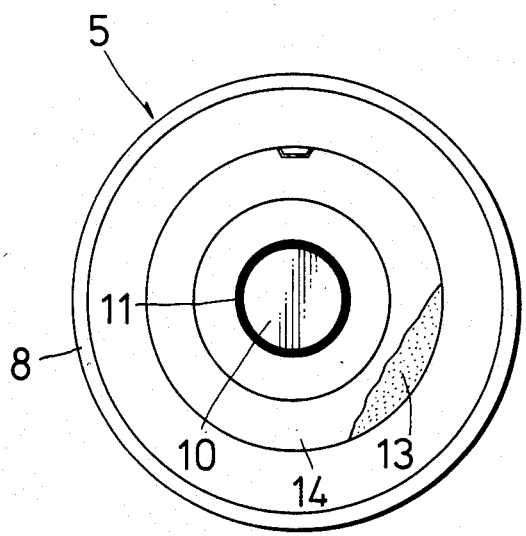
FIG. 5 is a plan view of the electrode of FIG. 4.

Since the construction of the electrodes 5, 6, 7 are identical, the construction of only electrode 5 will be described with reference to FIGS. 3, 4 and 5. The electrode 5 has a waterproof cup-shaped suction disc. A through hole 9 is perforated at the center of the disc 8, as shown in FIG. 4, and one end of the lead wire 2 is inserted from the conex side of the suction disc 8 into the hole 9 toward the concave side. An electrode plate 10 is connected to the end of the lead wire 2 and bonded to block the hole 9 at the concave side of the suction disc 8. The other ends of the lead wires 2, 3, 4 are connected to a connector 1 respectively, as shown in FIG. 3, and the wireless transmitter 15 with an antenna 16 is coupled to the connector.

The contacting portion between the outer periphery portion of the plate 10 and the concave surface of the suction disc 8 is hermetically sealed with elastic sealing material 11 such as silicone rubber; and the gap between the periphery of the wire 2 and the convex surface of the suction disc 8 is hermetically sealed with elastic sealing material 12 such as a silicone rubber, thereby preventing immersion in water from the outer surface of the suction disc 8. An annular, body surface adherent sheet 14 is bonded with adhesive 13 along the concentric circle surrounding the plate 10 on the concave surface of the suction disc 8, and the adhesive is coated also on the surface of the adherent sheet 14.

Figure 2:
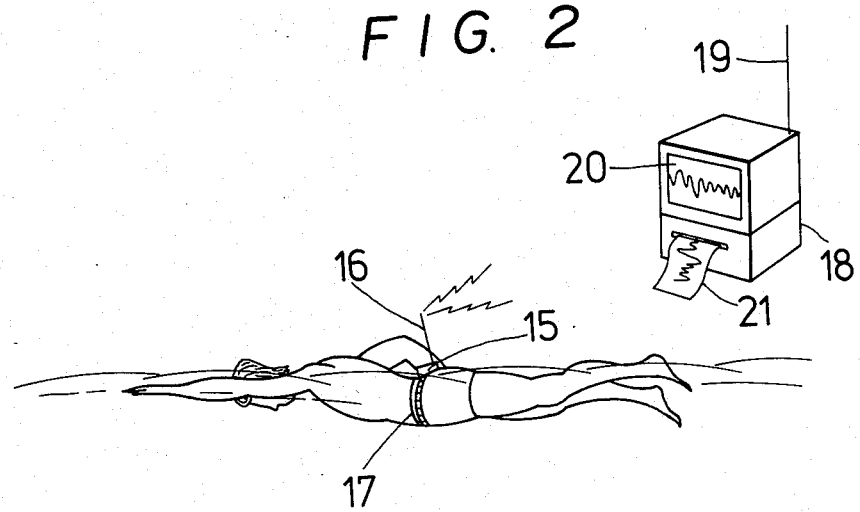
FIG. 2 is a view of a system for recording the electrocardiogram on the basis of the electrocardiac signal received remotely by radio wave.

Putting the electrodes 5, 6, 7 with the transmitter 15 on an examinee's body, and letting the examinee swim as shown in FIG. 2, the electrocardiac signal of the swimmer is detected by the electrode plate 10, and the signal which is detected by the electrode plate 10 is led through the wires 2, 3, 4 to the transmitter 15.

The electrocardiac signal led to the transmitter 15 is transmitted from an antenna 16, and the transmitted signal is remotely received by an antenna 19 of a receiver 18 placed on the ground. The received signal is indicated on a CRT 20, or recorded on a recording sheet 21 to be analyzed in the electrocardiogram.

As described above, according to the present invention, the electrocardiogram of a living body moving in the water can be recorded by detecting an electrocardiac signal of the living body by the electrodes, leading the detected electrocardiac signal through lead wires to a wireless transmitter mounted on the living body, receiving the radio electrocardiac signal transmitted from the transmitter by a receiver, and recording the electrocardiogram on the basis of the radio electrocardiac signal received by the receiver. Therefore, the electrocardiogram of the living body in swimming can be efficiently recorded without a cable.

Further, since a cable is not necessary, the current leakage phenomenon does not occur as a result, the electrocardiogram of the living body during swimming can be recorded accurately.

Furthermore, there is no possibility that a cable is entangled with hands and legs. Thus, the living body can freely swim, and the electrocardiogram can be recorded in any state of swimming motion.

While the present invention has been described in detail with respect to a certain preferred embodiment of the invention, it will be understood by those skilled in the art that various changes and modifications may be made without departing from the spirit and scope of the invention, and it is intended, therefore, to cover all such changes and modification in the appended claims.

What is claimed is:

1. A method of diagnosing the heart condition of a living body during exercise in water comprising the steps of:
    (a) providing at least one suction disc having mounted thereon a hermetically sealed electrode surrounded by an annular body surface adherent strip, said sealed electrode being in non-contacting circumferential relationship with said annular strip;
    (b) placing said suction disc with said hermetically sealed electrode on a living body to be moving in the water, the disc being held firmly to the moving body by vacuum forces effected from the suction disc and adhesive forces effected circumferentially around said sealed electrode due to said adherent strip;
    (c) detecting an electrocardiac signal from said hermetically sealed electrode while said body is moving in the water;
    (d) leading the detected electrocardiac signal from the electrode through lead wires to a radio transmitter mounted on the living body;
    (e) receiving the radio-transmitted electrocardiac signal by a receiver; and
    (f) recording an electrocardiograph derived from the signal received by the receiver.

* * * * *

UNITED STATES PATENT AND TRADEMARK OFFICE
CERTIFICATE OF CORRECTION

PATENT NO. : 4,791,933
DATED : December 20, 1988
INVENTOR(S) : Toshio Asai, et al.

It is certified that error appears in the above-identified patent and that said Letters Patent is hereby corrected as shown below:

In the Abstract, line 3, before "recorded" insert --is--.

In the Abstract, line 9, change "transmitted" (second occurrence) to --transmitter--.

Column 2, line 19, change "an explanatory" to --a--.

Column 2, line 19, change "for describing" to --of a system for carrying out--.

Column 2, line 25, after "showing" insert --a--.

Column 2, line 46, change "conex" to --convex--.

Signed and Sealed this

Twenty-fifth Day of April, 1989

Attest:

DONALD J. QUIGG

*Attesting Officer*       *Commissioner of Patents and Trademarks*